United States Patent [19]

Peers-Trevarton

[11] Patent Number: 4,469,104
[45] Date of Patent: Sep. 4, 1984

[54] MULTIPOLAR CONNECTOR FOR PACING LEAD

[75] Inventor: Charles A. Peers-Trevarton, Coral Springs, Fla.

[73] Assignee: Cordis Corporation, Miami, Fla.

[21] Appl. No.: 399,062

[22] Filed: Jul. 16, 1982

[51] Int. Cl.³ .............................................. A61N 1/00
[52] U.S. Cl. .................. 128/419 P; 128/786
[58] Field of Search .................... 128/419 P, 784–786; 334/60, DIG. 3

[56] References Cited

U.S. PATENT DOCUMENTS

| | | | |
|---|---|---|---|
| 3,924,639 | 12/1975 | Hess | 128/786 |
| 4,012,103 | 3/1977 | Lunquist | 128/419 P X |
| 4,033,355 | 7/1977 | Amundson | 128/419 P X |
| 4,259,962 | 4/1981 | Roers-Trevarton | 128/419 P |
| 4,262,982 | 4/1981 | Kenny | 128/419 P X |
| 4,379,462 | 4/1983 | Borkan et al. | 128/786 |

FOREIGN PATENT DOCUMENTS 3023191 12/1981 Fed. Rep. of Germany ... 128/419 P

*Primary Examiner*—Edward M. Coven
*Attorney, Agent, or Firm*—Henry W. Collins; Thomas R. Vigil

[57] ABSTRACT

The pacing lead assembly includes a multiconductor pacing lead including a plurality of wire conductors within a sheath of insulating material. A connector assembly surrounds the proximal end of the pacing lead and includes spaced apart metal bands on the sheath with each one of the wire conductors electrically connected to one of the metal bands. The connector assembly also includes insulating segments between the metal bands and a resilient conductive ring on each metal band adapted to make electrical connection with a metal ring in a socket in a pulse generator into which the connector assembly is inserted. The metal bands are spool-shaped with end flanges that provide means for retaining each resilient conductive ring in place on the metal band.

9 Claims, 7 Drawing Figures

MULTIPOLAR CONNECTOR FOR PACING LEAD

BACKGROUND OF THE INVENTION

1. Field of the Invention

The present invention relates to a multipolar connector assembly utilized in a pacing lead.

2. Description of the Prior Art

Multiple electrode cardiac pacing leads are well known and have been utilized for pacing both the atrial and ventricular chambers of the heart.

Cardiac stimulation requires a reliable means for connecting electrical signals from a pulse generator, or pacer, to a pre-selected region on the wall of the heart. For example, a certain type of cardiac pacing lead is connected to a pacer, extends into the heart, and is placed in contact with the inside wall of the right ventricle. This lead normally takes the form of a long, generally straight, flexible, insulated conductor having one end electrically connected to the pacer and the other end connected to an electrode. The electrode is placed in contact with the wall of the heart.

On the other hand, pacing leads which are used for stimulation of the atrium are generally formed in a J-shaped configuration so that when the lead is inserted through a blood vessel and into the heart, the lead may be positioned to curve up into the atrial cavity.

Heretofore, pacing leads have been utilized which include a multipolar electrode assembly at the distal end thereof and a connector at the proximal end thereof for connecting the lead to a pulse generator. An example of such a lead is disclosed in U.S. Pat. No. 4,236,525 which discloses a lead assembly for a body implantable tissue stimulator having two distal electrodes and proximal connectors that are coaxially and axially spaced for mating with corresponding stimulator output electrodes in a pulse generator.

The connectors heretofore utilized for connecting the proximal end of a multiconductor conductor pacing lead to a pulse generator such as the connectors disclosed in U.S. Pat. No. 4,236,525 have worked satisfactorily. However, due to recent devleopments in cardiac pacing technology, leads having multiple conductors but of the same diameter or a smaller diameter than unipolar and bipolar leads are necessary.

The present invention takes the form of a novel connector at the proximal end of the pacing lead which includes one or more spool-shaped metal bands about the proximal end of the pacing lead and connected to individual wire conductors of the lead with an elastic conductive ring positioned about the spool. The elastic conductive ring is adapted to contact a metal sleeve embedded in the side wall of a socket in a body portion of the pulse generator into which the connector is inserted.

Also as will be described in greater detail hereinafter, the multipolar electrode assembly at the distal end of the multiconductor pacing lead is constructed in such a way as to facilitate solid electrical contact between the ends of each wire conductor in the multiconductor lead and individual electrodes of the electrode assembly and in such a way as to take up a minimum of space thereby to enable a very compact minimum diameter electrode.

SUMMARY OF THE INVENTION

According to the invention, there is provided a pacing lead assembly comprising a multiconductor pacing lead and a connector assembly surrounding the proximal end of said multiconductor pacing lead, said multiconductor pacing lead having said proximal end and a distal end and including at least two wire conductors within a sheath of insulating material, and said connector assembly including at least one metal band, means for electrically connecting one wire conductor to said one metal band, insulating means on either side of said metal band, a resilient conductive ring resiliently received on said band for electrically connecting said metal band to a metal ring in a socket in a pulse generator into which said connector assembly is inserted, and said band comprising means for retaining said resilient conductive ring in place on said metal band and for preventing said ring from being moved axially off of said metal band on relative movement between said connector and the socket.

DESCRIPTION OF THE PREFERRED EMBODIMENTS

Figure 1:
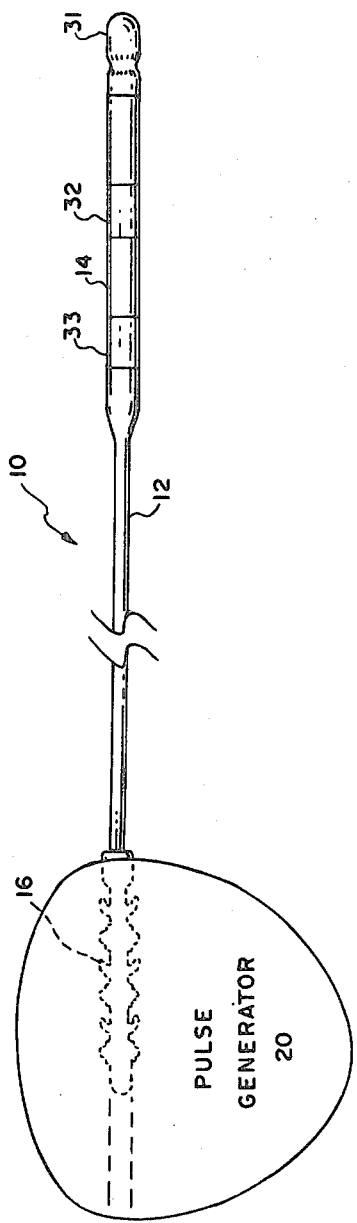
FIG. 1 is a side view of a pulse generator and pacing lead assembly which are constructed in accordance with the teachings of the present invention.

Referring now to FIG. 1 there is illustrated therein a pulse generator and pacing lead assembly 10 which includes a multiconductor pacing lead 12 having at its distal end a multipolar electrode assembly 14 and a multipolar insert connector 16 at the proximal end thereof which is received within a socket 18 (FIG. 3) formed in a body portion 19 (FIG. 3) in a pulse generator 20.

Figure 2:
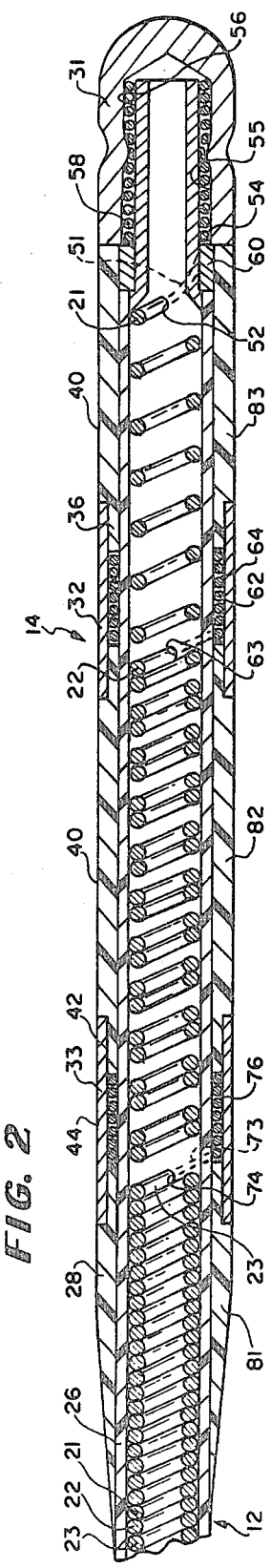
FIG. 2 is an enlarged sectional view of a multipolar electrode tip assembly which is mounted at the distal end of the pacing lead assembly shown in FIG. 1; and, FIG. 3 is an enlarged sectional view of the multipolar insert connector at the proximal end of the pacing lead assembly shown in FIG. 1 received in a socket in a body portion of the pulse generator shown in FIG. 1.

Referring now to FIG. 2 there is illustrated therein a cross section of the multiconductor pacing lead 12 and of the multipolar electrode assembly 14. As shown, the multiconductor pacing lead 12 includes three conductors or wires 21, 22 and 23 which are wound in a single coil.

The coiled conductors 21, 22 and 23 are surrounded by an insulating sheath 26 which can be made of silicone, polyurethane, or other insulating material, but preferably is formed of PARYLENE "C" manufactured by Union Carbide Corporation.

The distal end of the pacing lead 12 extends within an electrode body 28 made of an insulating material and which forms part of the multipolar electrode assembly 14. Mounted at the distal end of the body 28 is a first electrode 31 which can be referred to as a tip electrode 31. Then, spaced from the tip electrode 31 is a second sleeve electrode 32 and a third sleeve electrode 33 is spaced from the second sleeve electrode 32. The sleeve electrode 32 is received in an annular slot 36 formed in the body 28 so that outer facing surface 38 of the sleeve electrode 32 is flush with outer cylindrical surface 40 of the insulating body 28. Likewise, the second sleeve electrode 33 is an annular slot 42 in the insulating body 28 so that outer surface 44 thereof is flush with the cylindrical surface 40 of the insulating body 28.

Although not illustrated in FIG. 2, it is to be understood that each of the conductors or wires 21–23 has an insulating coating thereon so that it is insulated from the adjacent conductor.

As shown in FIG. 2, the first conductor 21 extends all the way to the first tip electrode 31 and an end portion 51 of the first conductor 21 extends through an opening 52 in the sheath 26. This end portion 51 is stripped of insulation and extends from the opening 52 in the sheath 26 through a slot (not shown) in the sheath 26 to an annular cavity 54 defined between an inner cylindrical surface 55 formed within the electrode 31 and outer surface 56 of a plug 58 which extends from the inner end of the sheath 26 around a ring 60 and into the cylindrical cavity 55. The electrode 31 is crimped at several points to retain the first conductor 21 between the outer surface 56 of the plug 58 and the inner cylindrical surface 55 of electrode 31 thereby to ensure a good electrical connection therewith.

In a similar manner, an end portion 62 of the second conductor or wire 22 is stripped of insulation so as to be a bare wire and extends through an opening 63 in the sheath 26 through a passageway in the sheath 26 to an annular passageway 64 where the bare conductor end portion 62 is coiled. The annular passageway 64 is defined between a thin layer (not shown) of electrode body 28 or the outer surface of the sheath 26 and the inner surface of the sleeve electrode 32. The width or thickness of the annular passageway 64 is such that the bare wire end portion 62 is urged against the inner surface of the sleeve electrode 32 thereby to ensure a good electrical contact therewith.

Further, and in like manner, the third conductor 23 has a bare end portion 73 which extends through an opening 74 in the sheath 26 and through a slot in the sheath 26 to an annular passageway 76 between a thin layer of the electrode body 28 or the outer surface of the sheath 26 and the inner surface of the third sleeve electrode 33. Also, the dimension or width of the annular passageway 76 is such that the bare conductor end portion 73 wound in a coil in the annular passageway 76 is urged against the inner surface of the sleeve electrode 33.

It will be appreciated from the foregoing description that the insulating body 28 which surrounds the distal end of the pacing lead 12 has been defined as one piece construction but is shown in FIG. 2 as being of three piece construction, namely of three elements 81, 82 and 83.

The multipolar electrode assembly 14, and in this particular instance, a three polar assembly 14, enables a physician to select any one of the three electrode 31, 32 or 33 for pacing the endocardium and for using any one of the electrodes 31, 32 and 33 for relaying information about selected tissue back to the pulse generator 20.

Figure 3:
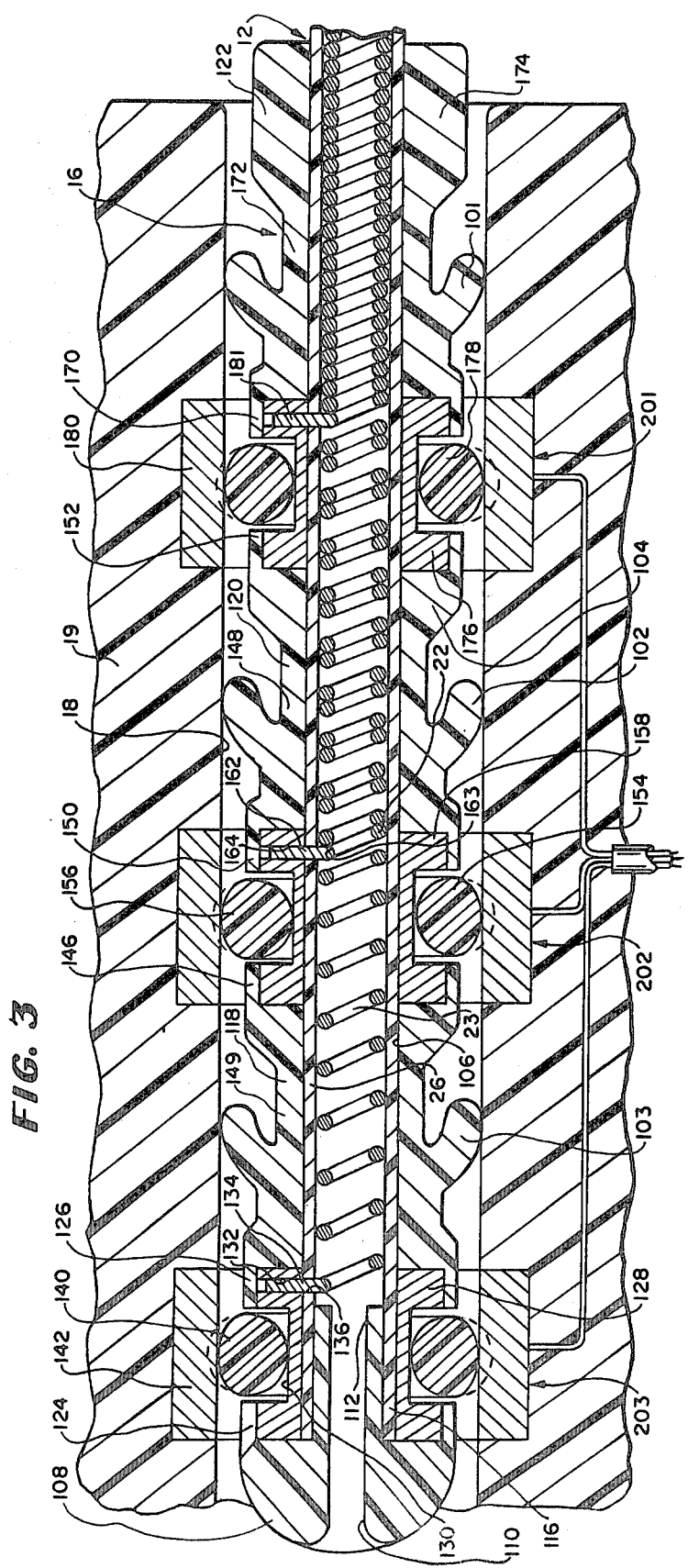

In FIG. 3 is illustrated the position of the insert connector 16 at the proximal end of the multiconductor pacing lead 12 received in the socket 18 in the body portion 19 of the pulse generator 20. As shown, the sidewall of the socket 18 is adapted to receive resilient flanges 101, 102 and 103 which extend from and are integral with an insulating body portion 104 of the insert connector 16. As shown in FIG. 3, when the insert connector 16 is inserted into the socket 18, the flanges 101, 102 and 103 will be flexed as shown for sealing the insert connector 16. Typically, the insulator body 104 and the flanges 101, 102 and 103 extending therefrom are made from an elastomeric insulating material such as silicone. The sealing arrangement shown in FIG. 3 is of the type shown in U.S. Pat. 4,259,962.

As shown in FIG. 3, the insulator body 104 has a central passageway 106 therein which is sized to receive the proximal end of the multiconductor pacing lead 12. The end 108 of the insulator body 104 of the insert connector 16 has a central passageway 110 therethrough which extends into the insulator body 104 and through a cylindrical protrusion 112 about which the proximal end 116 of the sheath 26 is received. This passageway 110 permits a stylet to be inserted through the passgeway 110 and the insulator body 104 into the coiled conductors 21, 22 and 23 within the sheath 26 of the multiconductor pacing lead 12.

Although the insulator body 104 has been described above as being of unitary construction, it is preferably, and as shown in FIG. 3, made of insulating body segments which include the end segment 108, two identical intermediate segments 118 and 120 and an outer end segment 122. The end segment 108 has an outer angular flange 124 extending inwardly and axially of the insert connector 16 and is spaced radially outwardly from the cylindrical protrusion 112.

The intermediate segment 18 has a similar annular flange 126 which extends toward the annular flange 124 so as to define an annular space, open in the middle, between the outer surface of the sheath 26 and the annular flanges 124 and 126. Received within this annular space is a spool-shaped metal band or ring 128 which has an annular slot 130 therein. The spool-shaped metal band 128 has a radial slot 132 therein which receives the bare end 134 of the conductor 23 which bare end 134 extends from the insulated conductor 23 through an opening 136 in the sheath 26.

Received within the slot 130 in the spool-shaped metal band 128 is a resilient ring 140 of conductive material which is adapted to electrically contact the slot 130 on its inwardly facing side and to electrically contact a metal ring 142 embedded in the body 19 and having an inwardly facing surface flush with the surface of the socket 18.

The conductive ring 140 is preferably made of a conductive resilient material such as silicon rubber. Also, as shown in FIG. 3, the ring 140 has a diameter which is greater than the space between the outer surface of the spool-shaped metal band 128 and the metal ring 142 embedded in the body 19 and having an inner surface flush with the surface of the socket 18 so that the ring 140 will be squeezed when the insert connector 16 is inserted into the socket 18. This is brought out in FIG. 3 by the showing of the normal unsqueezed position of the ring in phantom in FIG. 3.

Figure 4:
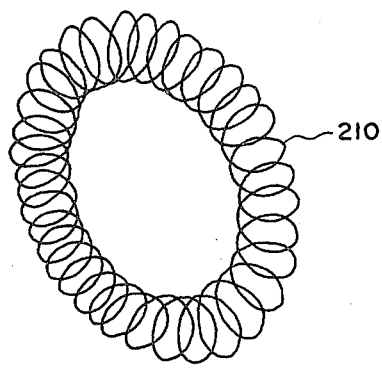
FIG. 4 is a perspective view of a conductive resilient garter spring.
Figure 5:
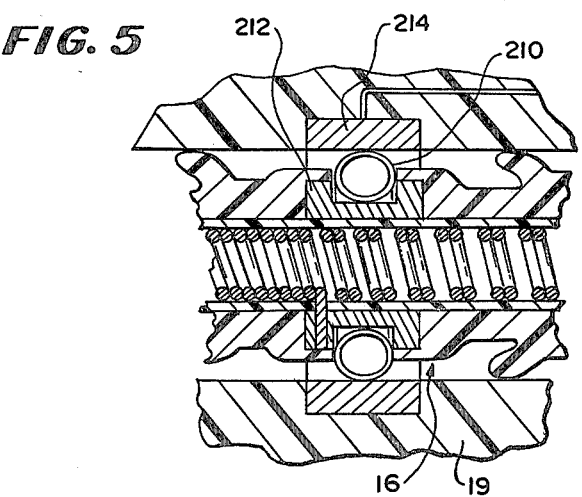
FIG. 5 is a fragmentary sectional view of a connector assembly utilizing the garter spring shown in FIG. 4.

It is to be understood that the conductive ring 140 can also be made of other materials. For example, it could be a so-called garter spring which is a coiled spring in which two ends are brought together and welded so as to form a toroid envelope which can be squeezed when the insert connector 16 is inserted into the socket 18. Such a coiled spring is shown in FIGS. 4 and 5 and will be described in greater detail hereinafter in connection with the description of FIGS. 4 and 5.

Figure 6:
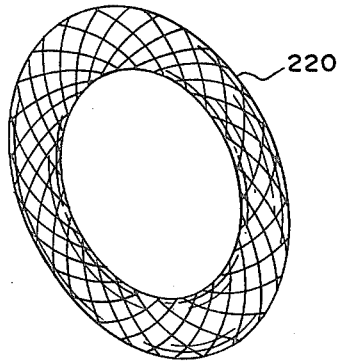
FIG. 6 is a perspective view of a toroid made of woven metal wire.
Figure 7:
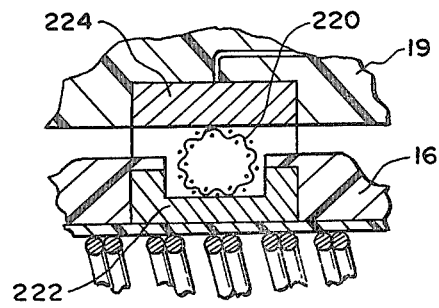
FIG. 7 is a fragmentary sectional view of a connector assembly showing the use of the woven metal wire toroid shown in FIG. 6.

Another type of conductive ring would be a ring made of woven metal. In this respect, a flat sheet of woven metal could be rolled into a roll and then the roll formed into a toroid with the ends welded together, thereby to form a resilient ring 140. As is apparent, there are numerous other conductive materials and configurations thereof which could be utilized to form the conductive ring 140. Such a toroid of woven metal is shown in FIGS. 6 and 7 and will be described in greater detail hereinafter in connection with the description of FIGS. 6 and 7.

The insulator segment 118 in addition to having the radially extending annular flange 103 and the axially extending annular flange 126 has a reduced-in-diameter portion 144 for facilitating flexing of the flange 103 when the insert connector 16 is inserted into the socket 18. Further, the segment 118 has another axially extending annular flange 146 as shown.

The insulator segment 120 is identical to the insulator segment 118 and in addition to having a radially extending flange 102, it has a reduced-in-diameter portion 148 and annular flanges 150 and 152. The insulator segment 120 is positioned on the sheath 26 such that the annular flanges 150 and 146 form with the outer surface of the sheath 26 an annular space, open in the middle, for receiving a conductive resilient ring 154 which makes contact with a metal ring 156 embedded in the side wall of the socket 18 in the body portion 19 and the exposed surface of a spool-shaped metal band 158 received in the annular space. A bare end 162 of conductor 22 extends through an opening 163 in the sheath 26 and is received in a slot 164 in the spool-shaped metal band 158 for making electrical contact therewith. In this way as in the previous electrical connection described above, electrical contact is effected between the end 162 of the conductor 22 through the metal band 158 and resilient conductive ring 154 to metal ring 156.

The insulator segment 122 is similar in construction to insulator segments 118 an 120 by having an axially extending annular flange 170 at one end thereof, the radially extending flange 101 and a reduced-in-diameter section 172. The outer end of segment 122 is a solid body 174, as shown, which is received about the multiconductor pacing lead 12.

The opposed ends of the insulator segments 120 and 122 form an annular space for receiving a spool-shaped metal band 176 which has a conductive ring 178 extending thereabout and adapted to make electrical contact with a metal ring 180 embedded in the side wall of the socket 18 as shown. Also, a bare end 181 of conductor 21 extends through the sheath 26 where it is rigidly fixed into a slot in the spool-shaped metal band 176 to ensure a good electrical contact therewith.

It will be understood that the radially extending flanges 101, 102 and 103 can be sized and configured to sealingly fit against the side wall of the socket 18.

With the construction of the insert connector 16 and the socket 18 as described above, three electrical connector assemblies, 201, 203 and 204 are created for facilitating good electrical connection between the ends 134, 162 and 181 of the conductors 23, 22 and 21 to the pulse generator circuitry (not shown) within the pulse generator 20.

In FIG. 4 is shown a coiled endless garter spring 210 which may be inserted into each of the asemblies 201, 202, and 203 in place of the resilient conductive rings 140, 154 and 178. Such a construction is shown in FIG. 5 where the resilient garter spring 210 is shown between a spool shaped metal band 212 on the insert connector 16 and a metal band 214 embedded in the body 19.

In FIG. 6 is shown a resilient toroid 220 which is made from a piece of woven metal wire which is first rolled into a tube and then coiled into a toroid and fixed at the mating ends thereof to form the toroid 220 shown in FIG. 6. This toroid 220 can then be used in place of the resilient conductive rings 140, 154 and 178 in the connector assemblies 201, 202 and 203. In FIG. 7 the toroid 220 is shown between a spool shaped metal band 222 mounted on the connector 16 and a metal band 224 embedded in the body 19.

From the foregoing description it will be apparent that the pacing lead assembly of the present invention made according to the method of the present invention has a number of advantages, some of which have been described above and others of which are inherent in the invention. Also it will be apparent to those skilled in the art that modifications can be made to the pacing lead of the present invention without departing from the teachings of the present invention. Accordingly, the scope of the invention is only to be limited as necessitated by the accompanying claims.

I claim:

1. A pacing lead assembly comprising a multiconductor pacing lead and a connector assembly surrounding the proximal end of said multiconductor pacing lead, said multiconductor pacing lead having said proximal end and a distal end and including at least two wire conductors within a sheath of insulating material, and said connector assembly including at least one metal band, means for electrically connecting one wire conductor to said one metal band, insulating means on either side of said metal band, a resilient conductive ring resiliently received on said band for electrically connecting said metal band to a metal ring in a socket in a pulse generator into which said connector assembly is inserted, and said band comprising means for retaining said resilient conductive ring in place on said metal band and for preventing said ring from being moved axially off of said metal band on relative movement between said connector and the socket.

2. The connector assembly of claim 1 wherein said insulating means include at least one insulator segment having at least one radially extending resilient flange which is adapted to be flexed when said connector assembly is inserted into the socket of the pulse generator.

3. The connector assembly of claim 1 wherein said conductive ring is made of conductive silicone elastomer.

4. The connector assembly of claim 1 wherein said conductive ring is made of a coiled garter spring.

5. The connector assembly of claim 1 wherein said conductive ring is made of woven metal fabric which is coiled into a cylinder and the cylinder is then welded at the ends to form a toroid.

6. The connector assembly of claim 1 wherein an insulator segment is provided at the proximal end of said connector assembly and has an axial passageway therethrough communicating with the interior of said pacing lead.

7. The connector assembly of claim 1 wherein each of said metal bands is spool-shaped and has a central cylindrical portion and end flanges which define said retaining means.

8. The connector assembly of claim 7 wherein each spool-shaped metal band has a radially extending slot therein for frictionally receiving the bare end of one of said wire conductors which extends through an opening in the sheath into said radially extending slot.

9. The connector assembly of claim 1 including two additional bands and two additional resilient conductive rings, each positioned on one of said additional metal bands, and wherein all of said bands are spaced from each other, and said insulating means insulate said metal bands from each other.

* * * * *